(12) United States Patent
Yeager et al.

(10) Patent No.: US 9,139,350 B2
(45) Date of Patent: Sep. 22, 2015

(54) ANTI-STATIC PACKAGE FOR MEDICAL CONTAINERS

(71) Applicant: West Pharmaceutical Services, Inc., Exton, PA (US)

(72) Inventors: Ricky Yeager, Douglassville, PA (US); Rohit Vora, Newark, CA (US); William D. Knaup, Boyertown, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 71 days.

(21) Appl. No.: 14/156,876

(22) Filed: Jan. 16, 2014

(65) Prior Publication Data
US 2015/0197387 A1    Jul. 16, 2015

(51) Int. Cl.
| | |
|---|---|
| B65D 83/10 | (2006.01) |
| B65D 81/20 | (2006.01) |
| B65D 21/02 | (2006.01) |
| B65D 51/18 | (2006.01) |
| B65D 25/10 | (2006.01) |
| B65D 85/00 | (2006.01) |

(52) U.S. Cl.
CPC .......... B65D 81/20 (2013.01); B65D 21/0233 (2013.01); B65D 25/108 (2013.01); B65D 51/18 (2013.01); B65D 85/70 (2013.01)

(58) Field of Classification Search
CPC .......... A61M 2209/06; A61M 25/002; A61M 5/005; A61B 19/0271; A61B 19/0256; H05K 9/0067
USPC .......... 206/210, 363–366, 571, 209, 219, 220
See application file for complete search history.

(56) References Cited

U.S. PATENT DOCUMENTS

| | | | |
|---|---|---|---|
| 4,774,272 A | 9/1988 | Lamphere et al. | |
| 5,097,949 A * | 3/1992 | Heldwein | 206/720 |
| 5,202,098 A * | 4/1993 | Nichols | 422/300 |
| 6,073,767 A * | 6/2000 | Cohen et al. | 206/363 |
| 6,164,044 A * | 12/2000 | Porfano et al. | 53/471 |
| 7,428,807 B2 | 9/2008 | Vander Bush et al. | |
| 7,963,396 B2 | 6/2011 | Vanderbush et al. | |
| 8,100,263 B2 | 1/2012 | Vanderbush et al. | |
| 2006/0186010 A1 | 8/2006 | Warnack et al. | |
| 2007/0151882 A1* | 7/2007 | Cocheteux et al. | 206/366 |
| 2007/0160786 A1* | 7/2007 | Levin et al. | 428/35.2 |
| 2009/0321283 A1* | 12/2009 | Tourigny | 206/205 |
| 2014/0027326 A1* | 1/2014 | Peruzzo | 206/364 |
| 2014/0353190 A1* | 12/2014 | Okihara et al. | 206/370 |

FOREIGN PATENT DOCUMENTS

| | | | |
|---|---|---|---|
| WO | 2006088874 A2 | 8/2006 | |
| WO | 2010001130 A2 | 1/2010 | |

\* cited by examiner

*Primary Examiner* — Jacob K Ackun
*Assistant Examiner* — Rafael Ortiz
(74) *Attorney, Agent, or Firm* — Panitch Schwarze Belisario & Nadel LLP

(57) ABSTRACT

A package for storing a plurality of medical containers includes a housing having a closed base end and an open upper end. A nesting tray is at least partially supported by the housing, and has a plurality of apertures for receiving, and supporting, the medical containers. A protective slip sheet is provided within the housing. A static shield for dissipating static charge within the housing is also provided. The package also includes a housing cover.

18 Claims, 2 Drawing Sheets

ANTI-STATIC PACKAGE FOR MEDICAL CONTAINERS

BACKGROUND OF THE INVENTION

The present invention relates generally to a package for medical containers and, more particularly, to an anti-static container/package for receiving and storing medical containers.

Sterile filling of medicament into sterile medical containers is generally automated and conducted in a sterile or aseptic facility, such as a clean room, in order to minimize the possibility of medicament contamination. Open, empty medical containers are typically sterilized and placed into sealed sterile packages, such as boxes or tubs, by a manufacturer prior to shipping to a filling destination. The tubs support the medical containers therein in a secure and orderly manner, such that upon arrival at the filling destination, robots or other machines can perform an automated sterile filling procedure. For example, the robots or machines re-sterilize the exterior of the shipped tubs prior to entry into the filling room, transport the sterilized tubs into the room, open the sealed tubs, remove any protective contents from the tubs, remove the containers from the tubs and fill the containers with the necessary medicament.

Throughout the filling process, the medical containers must remain sterile prior to the introduction of sterile medicament therein, such that the introduced medicament does not become contaminated. Thus, typically, a protective slip sheet is placed atop the open ends of the medical containers within the tubs, in order to protect the containers from loose particles that may fall into the medical containers during opening of the tubs. Otherwise, contaminating the containers with the particles ultimately contaminates the medicament filled therein. The protective slip sheets also shield the underlying medical containers from potentially hazardous radiation, such as, for example, electron beam radiation within a filling room.

One drawback of the tubs, however, is that movement of the contents therein during shipping can create a static charge within the tub. Such a static charge may attract particles during the automated removal of the cover sheet, increasing the likelihood of medical container contamination. Such a static charge may also cause the protective sheet to stick to, and be removed with, the cover sheet during automated removal of the cover sheet. Thereafter, when a robot or machine, configured to remove the protective slip sheet, does not find the sheet in the tub as expected, the automated system shuts down or malfunctions, delaying the filling process and requiring human intervention. Accordingly, it would be advantageous to ship the medical containers in a tub that generally does not create, or at least dissipates, a static charge which may build up in the package, thereby alleviating or at least minimizing the problems associated with a static charge.

BRIEF SUMMARY OF THE INVENTION

Briefly stated, one aspect of the present invention is directed to a package for storing a plurality of medical containers. The package includes a housing having a closed base end and an open upper end. A nesting tray is at least partially supported by the housing, and has a plurality of apertures for receiving, and supporting, the medical containers. A protective slip sheet is provided within the housing. A static shield for dissipating static charge within the housing is also provided. The package also includes a housing cover.

In accordance with another aspect, the present invention is directed to a package for storing a plurality of medical containers. The package includes a housing having a closed base end and an open upper end. A nesting tray is at least partially supported by the housing, and has a plurality of apertures for receiving, and supporting, the medical containers. A protective slip sheet is provided within the housing. The protective slip sheet includes a static shield for dissipating static charge within the housing. The package also includes a housing cover.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
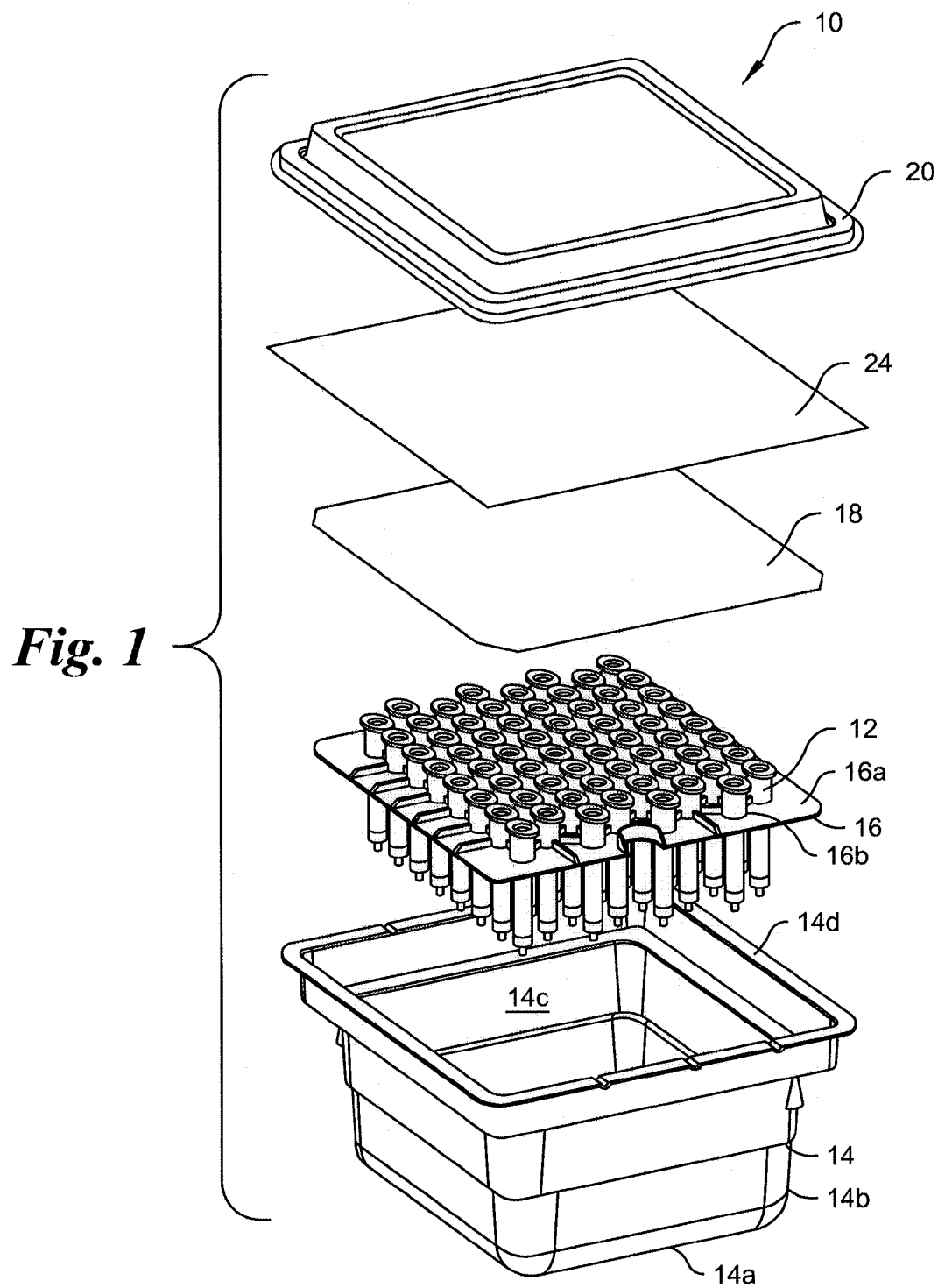
FIG. 1 is an exploded perspective view of a package for medical containers according to a preferred embodiment of the present invention.

Certain terminology is used in the following description for convenience only and is not limiting. The words "bottom" and "top" designate directions in the drawings to which reference is made. Hereinafter, the terms "proximal" and "rear" are synonyms, as are the terms "distal" and "front." The word "inwardly" and "outwardly" refer to directions toward and away from, respectively, the geometric center of the device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Figure 2:
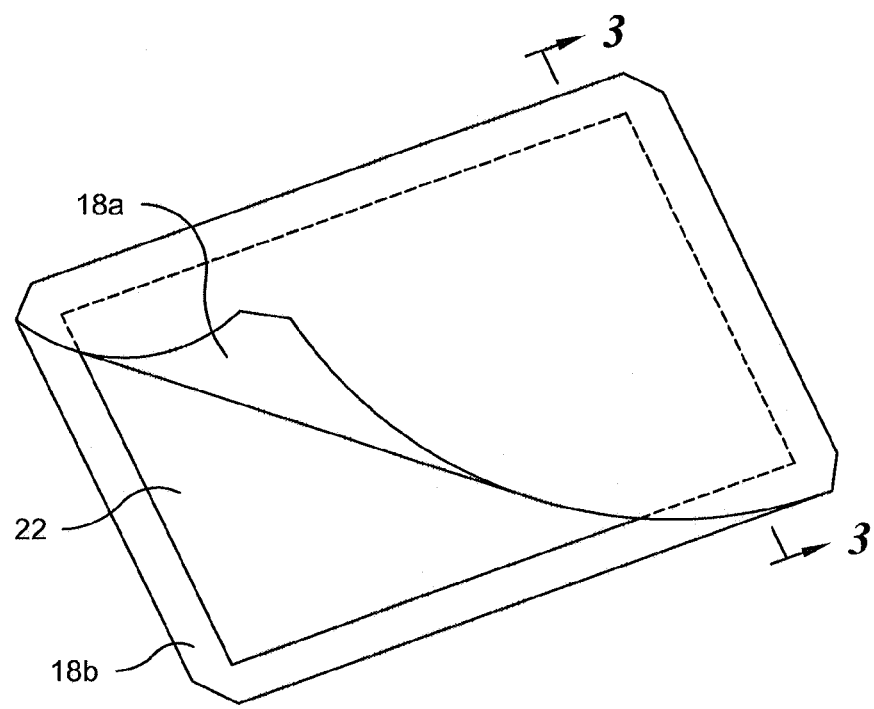
FIG. 2 is a perspective top view of a partially opened protective slip sheet of the package of FIG. 1, illustrating a preferred static shield.
Figure 3:
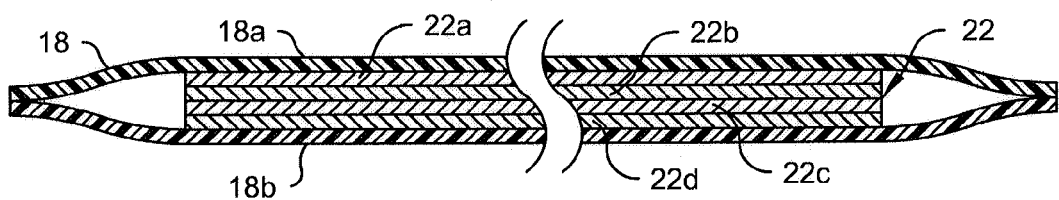
FIG. 3 is a cross-sectional view of a protective slip sheet, taken along line 3-3 of FIG. 2, showing a multiple layer static shield.

Referring to the drawings in detail, wherein the same reference numerals indicate the same components through the figures, there is shown in FIGS. 1-3 a package, generally designated 10, for receiving and transporting a plurality of medical containers 12. In the illustrated embodiment, the medical containers 12 are syringes or syringe barrels. However, as should be understood by those of ordinary skill in the art based on the teachings herein, the medical containers may be any of numerous different containers or vessels that are transported from a medical container manufacturer to a filling destination. For example, and without limitation, the medical containers 12 may be vials or test tubes.

The package 10 includes a housing or tub 14, a nesting tray 16, a protective slip sheet 18, a cover sheet 24 and a lid or housing cover 20. As shown in FIG. 1, the housing 14 includes a bottom or base wall 14a, defining a closed base or bottom end, and four adjoining sidewalls 14b (or one continuous sidewall) extending upwardly from the base wall 14a. The base wall 14a and sidewalls 14b define an internal cavity 14c and an open upper end having a generally flat rim 14d on the upper surface of the sidewalls 14b. The housing 14 is dimensioned to receive and at least partially support the nesting tray 16 at a predetermined distance above the closed base end 14a of the package 10 so that medical containers 12 supported by the nesting tray 16 do not engage the closed base end 14a. As should be understood by those of ordinary skill in the art, the housing 14 may be constructed of a polymeric material or any other suitable material. In the illustrated embodiment, the housing 14 defines a generally square or rectangular shape. However, as should be understood by those of ordinary skill in the art, the housing 14, tray 16, slip sheet 18, cover sheet 24 and cover 20 may define any of numerous other shapes, such as, for example, and without limitation, a cylindrical or other shape.

The tray 16 is removably nested into the housing 14 and supports the plurality of medical containers 12. In the embodiment shown in FIG. 1, the housing sidewalls 14a define a generally continuous stepped portion 14e proximate to the rim 14d as a support surface for receiving and supporting the tray 16. The tray 16 includes a laterally directed surface 16a having a plurality of spaced apertures 16b for receiving and supporting the medical containers 12. When the medical containers 12 project through the apertures 16b, handles or flanges of the medical containers 12 engage and rest against the surface 16a surrounding the respective apertures 16b and are supported thereby. In the illustrated embodiment, the apertures 16b are arranged in a series of uniformly spaced rows and columns. However, as should be understood, the apertures 16b may be arranged and spaced in any of numerous different patterns, or even randomly. The apertures 16b are sufficiently spaced from the periphery of the surface 16a, such that the perimeter of the surface 16a defines lateral flanges for resting atop the support surface 14e. Alternatively, the nesting tray 16 may be supported in the housing 14 in some other manner if desired. For example, two or more legs (not shown) may extend down from the undersurface of the nesting tray 16 for engaging the base wall 14a.

In the illustrated embodiment, the protective slip sheet 18 is positioned in the housing 14 above, or on top of, the upper surface of the medical containers 12 to cover the medical containers 12 and the nesting tray 16. However, the protective slip sheet 18 could be located at some other place in the housing 14, such as, for example, proximate to the rim 14d or between the rim 14d and the top of the medical containers 12. As shown, the protective sheet 18 has substantially equal dimensions to those of the lateral surface 16a of the tray 16. In some embodiments, the protective sheet 18 is constructed of a gas permeable material, such as, for example, a flashspun high-density polyethylene sold under the trademark TYVEK by E.I. DuPont & Co. For example, a TYVEK 1073B sheet may be utilized. However, as should be recognized by those of ordinary skill in the art, the protective sheet 18 may be constructed of any other, preferably gas permeable material, currently known or that later becomes known, and which is capable of performing the functions of the protective slip sheet 18 as described herein.

In the present embodiment, as shown in FIG. 2, the protective slip sheet 18 includes a top layer 18a and a bottom layer 18b, with an intermediate static shield 22 of a type well known in the art therebetween. The top and bottom layers 18a, 18b, may be sealed together along the peripheries to enclose the static shield 22 therebetween. In other embodiments (not shown), the static shield 22 may be separate from the protective sheet 18 and may be positioned in the housing 14 above or below the protective sheet 18.

In some embodiments, the static shield 22 includes multiple layers having static dissipative properties to provide multiple layers of protection. As shown in FIG. 3, for example, the static shield 22 may include four static dissipative layers between the top and bottom layers 18a, 18b: a top layer 22a, an upper middle layer 22b, a lower middle layer 22c and a base layer 22d. In some embodiments, the four-layer static shield 22 includes a first static dissipative layer 22a, a polymeric layer 22b, a metallic shield layer 22c, and a second static dissipative layer 22d, such as is sold by Uline, Inc. In some such embodiments, the top layer 22a is a static dissipative coating layer, the upper middle layer 22b is a polyester layer, the lower middle layer 22c is an aluminum shield layer, and the base layer 22d is a static dissipative polyethylene layer. As should be understood by those of ordinary skill in the art, however, the arrangement and materials of the layers 22a, 22b, 22c and 22d may vary for a particular application.

As shown in FIG. 1, the housing cover 20 engages the open upper end of the housing 14 to provide a tight interference fit after the nesting tray 16 with the supported containers 12 and the protective slip sheet 18 are inserted therein. In some embodiments, the cover 20 is configured to removably attach to the housing rim 14d via a snap-fit. However, as should be understood by those of ordinary skill in the art, the housing cover 20 may removably cover the housing 14 via any of numerous different attachment means currently known, or that later become known.

As shown in FIG. 1, the package 10 may also include a separate cover sheet 24 positioned between the protective slip sheet 18 and the housing cover 20 to seal the open upper end of the housing 14. The cover sheet 24, which is at least slightly larger than the open upper end of the housing 14, is removably adhered or sealed to the housing rim 14d, via any of numerous removable adhering methods known in the art, such as, for example, heat sealing, thereby sealing the cavity 14c and the contents therein from the atmosphere. In some embodiments, the cover sheet 24 is also constructed of a high-density polyethylene or a polyolefin sold under the trademark TYVEK by E.I. DuPont & Co.

As should be understood by those of ordinary skill in the art, the static shield 22 is configured to dissipate static charge, i.e., reduce static electricity buildup, within the package assembly 10 during storage, shipment or other movement. Thus, during assembly, shipping, handling, opening of the package, and during the filling process, the buildup of static electricity is mitigated. Accordingly, for example, during an automated filling process, a decreased amount of particles will be attracted to the package 10 when the cover sheet 24 is removed from the housing 14, thereby reducing the chance of contamination of the medical containers 12. Additionally, the protective sheet 18 does not stick to the cover sheet 24 as it is removed. Therefore, a machine or robot configured to remove the protective sheet 18 will find the protective sheet 18 located on or above the containers 12, thereby reducing the possibility of shut down or malfunction of the automated filling system.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A package for storing a plurality of medical containers comprising:
   a housing having a closed base end and an open upper end;
   a nesting tray at least partially supported by the housing, and having a plurality of apertures for receiving, and supporting, the medical containers;

a protective slip sheet within the housing,
a static shield for dissipating static charge within the housing; and
a housing cover.

2. The package as defined in claim 1, wherein the static shield comprises multiple layers.

3. The package as defined in claim 2, wherein the static shield comprises a first static dissipative layer, a polymeric layer, a metallic shield layer and a second static dissipative layer.

4. The package as defined in claim 3, wherein the first static shield layer is a static dissipative coating layer, the polymeric layer is a polyester layer, the metallic shield layer is an aluminum layer and the second static dissipative layer is a polyethylene layer.

5. The package as defined in claim 1, wherein the protective slip sheet comprises a gas permeable material.

6. The package as defined in claim 1, further comprising a cover sheet positioned proximate the open upper end of the housing for sealing the open upper end of the housing.

7. The package as defined in claim 6, wherein the cover sheet is adhered to an upper rim proximate to the upper end of the housing.

8. The package as defined in claim 1, wherein the housing cover is adapted to engage and cover the upper end of the housing.

9. The package as defined in claim 1, further comprising a plurality of medical containers.

10. A package for storing a plurality of medical containers comprising:
a housing having a closed base end and an open upper end;
a nesting tray at least partially supported by the housing, and having a plurality of apertures for receiving, and supporting, the medical containers;
a protective slip sheet within the housing, the slip sheet including a static shield for dissipating static charge within the housing; and
a housing cover.

11. The package as defined in claim 10, wherein the static shield comprises multiple layers.

12. The package as defined in claim 11, wherein the static shield comprises a first static dissipative layer, a polymeric layer, a metallic shield layer and a second static dissipative layer.

13. The package as defined in claim 12, wherein the first static shield layer is a static dissipative coating layer, the polymeric layer is a polyester layer, the metallic shield layer is an aluminum layer and the second static dissipative layer is a polyethylene layer.

14. The package as defined in claim 10, wherein the protective slip sheet comprises a gas permeable material.

15. The package as defined in claim 10, further comprising a cover sheet positioned proximate the open upper end of the housing for sealing the open upper end of the housing.

16. The package as defined in claim 15, wherein the cover sheet is adhered to an upper rim proximate to the upper end of the housing.

17. The package as defined in claim 10, wherein the housing cover is adapted to engage and cover the upper end of the housing.

18. The package as defined in claim 10, further comprising a plurality of medical containers.

* * * * *